US006756504B2

(12) United States Patent
Dagan et al.

(10) Patent No.: US 6,756,504 B2
(45) Date of Patent: Jun. 29, 2004

(54) SPHINGOLIPIDS

(75) Inventors: Arieh Dagan, Jerusalem (IL); Shimon Gatt, Jerusalem (IL)

(73) Assignee: Yissum Research Development Company of the Hebrew University of Jerusalem, Jerusalem (IL)

(*) Notice: Subject to any disclaimer, the term of this patent is extended or adjusted under 35 U.S.C. 154(b) by 0 days.

(21) Appl. No.: 10/273,664

(22) Filed: Oct. 17, 2002

(65) Prior Publication Data

US 2003/0133904 A1 Jul. 17, 2003

Related U.S. Application Data

(63) Continuation of application No. PCT/IL01/00909, filed on Sep. 26, 2001, and a continuation-in-part of application No. PCT/IL01/00361, filed on Apr. 18, 2001.
(60) Provisional application No. 60/198,513, filed on Apr. 19, 2000.

(51) Int. Cl.$^7$ ............................................. C07C 233/00
(52) U.S. Cl. ........................... 554/52; 554/55; 558/166; 564/305; 564/188; 568/939; 514/623; 514/642; 514/645; 514/660; 514/661
(58) Field of Search .................. 554/52, 55; 558/166; 564/188, 305; 568/939; 514/623, 642, 645, 660, 661

(56) References Cited

FOREIGN PATENT DOCUMENTS

| EP | 0072286 | 2/1983 |
|---|---|---|
| EP | 0398340 | 11/1990 |
| EP | 398340 | 11/1990 |
| WO | WO 9843676 | 10/1998 |
| WO | WO 0179152 | 10/2001 |

OTHER PUBLICATIONS

Bose et al., Ceramide Synthase Mediates Daunorubicin–Induced Apoptosis: An Alternative Mechanism for Generating Death Signals, Cell 82, 405–414 (1995) (Exhibit 4).
Hannun et al., Sphingolipid breakdown products: anti–proliferative and tumor–suppressor lipids, Bicohim. Biophys. Acta 1154. 223–236 (1993); (Exhibit 5).
Higgins et al., Is the multidrug transporter a flippase?, Trends Biochem. Sci 17, 18–21 (1992); (Exhibit 6).
Karasavvas et al., Stereospecific induction of apoptosis in U937 cells by N–octanoyl–sphingosine stereoisomers and N–octyl–sphingosine, Eur. J. Biochem. 236, 723–731 (1996); (Exhibit 7).
Naoya M. et al., Quantitative Measurement of Sphingosine 1–1–Phosphate by Radiorreceptor–Binding Assay, (2000) Analytical Biochemistry 282, p. 115–120; (Exhibit 8).
Nicholson et al., Preferential killing of multidrug–resistant KB cells by inhibitors of glucosylceramide synthase, British J. Cancer 81, 423–430 (1989); (Exhibit 9).

(List continued on next page.)

*Primary Examiner*—Deborah D. Carr
(74) *Attorney, Agent, or Firm*—John P. White; Cooper & Dunham LLP

(57) ABSTRACT

The invention relates to compounds of the general formula (I), as defined, and to pharmaceutical compositions containing them.

The compounds of formula (I) are inhibitors of various lipid-related enzymes. They can be used in reducing accumulation of sphingolipids and thus in the treatment of lipid storage diseases.

The compounds of formula (I) can also be used for the treatment of cancerous diseases and for killing of wild type and drug-resistant cancer cells.

21 Claims, 5 Drawing Sheets

OTHER PUBLICATIONS

Suzuki et al, Sequential Operation of Ceramide Synthesis and ICE Cascade in CPT–11–Initiated Apoptotic Death Signaling, Exp. Cell Res. 233, 41–47 (1997); (Exhibit 10).
Weider et al., Induction of Ceramide–mediated Apoptosis by the Anticancer Phospholipid Analog, Hexadecylphosphocholine, J. Biol. Chem. 273, 11025–11031 (1998). (Exhibit 11).
Bielawska et al., *J. Biol. Chem.* 271, 12646–12654 (1996) (exhibit 2).
Bielawska et al., *J. Biol. Chem.* 267, 18493–18497 (1992) (exhibit 3).
Cabot et al., FEBS Letters 394, 129–131 (1996) (exhibit 4).
Cabot et al., *FEBS Letters* 431, 185–199 (1998) (exhibit 5).
Cox et al., *The Lancet* 355, 1481–1485, (2000) (exhibit 6).
Cravedi, J.P. et al. (1995) *Chem. Res. Toxicol.* 8, pp. 642–648 (exhibit 7).
Database Crossfire Beilstein, (1952) *Pharmazie.* 4, p. 693, XP002197316 (exhibit 8).
Database Crossfire Beilstein, (1954) *Pharmazie.* 19, p. 593, XP002197314 (exhibit 9).
Database Crossfire Beilstein, (1971) *Pharmazie.* 20, p. 403, XP002197315 (exhibit 10).
Database Crossfire Beilstein, (1972) *Pharmazie.* 27, pp. 148–153, XP002197312 (exhibit 11).
Database Crossfire Beilstein, (1997) Pharmazie. 86, pp. 1173–1179, XP002197313 (exhibit 12).
Endo et al., *Cancer Research* 51, 1613–1618, (1991) (exhibit 13).
Gomez–Munoz, A., *Biochim. Biophys. Acta* 1391, 92–109 (1998) (exhibit 14).
Hannun et al., *Trends Cell Biol.* 10, 73–80 (2000) (exhibit 15).
Hyun et al., (1975) *Archives of Biochemistry & Biophysics.* 166, pp. 382–389 XP001040386 (exhibit 16).
Lavie et al., *J. Biol. Chem.* 271. 19530–19536 (1996) (exhibit 17).
Lavie et al., *J. Biol. Chem.* 272, 1682–1687 (1997) (exhibit 18).
Levade et al., *Biochim. Biophys. Acta* 1438, 1–17 (1999) (exhibit 19).
Liu et al., *J. Biol Chem.* 274, 1140–1146 (1999) (exhibit 20).
Lucci et al., *Cancer* 86, 300–311 (1999) (exhibit 21).
Luckenbach, R. (1985) Beilsteins Handbuch der Organischen Chemie. vol. XIII, p. 2776, XP002197733 (exhibit 22).
Mathias et al., *Biochem. J.* 335, 465–480 (1998) (exhibit 23).
Maurer et al, *J. Natl. Cancer Inst.* 91, 1138–1146 (1999) (exhibit 24).
Perry et al, *Biochim. Biophys. Acta.* 1436, 233–243 (1998) (exhibit 25).
Raisova, M. et al. (2002) *FEBS Letters.* 516, pp. 47–52, XP004349046 (exhibit 26).
Riboni et al., *Prog. Lipid Res.* 36, 153–195 (1997) (exhibit 27).
Strum et al., *J. Biol. Chem.* 269, 15493–15497 (1994) (exhibit 28).
Szulc, Z.M. et al., (2000) *Tetrahedron Letters.* 41, pp. 7821–7824, XP004235879 (exhibit 29).
Vunnam, R.R. et al. (1979) *Biochim. Biophys. Acta* 26. 573, pp. 73–82, XP002944323 (exhibit 30).
Vunnam & Radin, *Chem. Phys. Lipid* 26, 265–278 (1980) (exhibit 31).
Warren, KR. et al. (1976) *Journal of Neurochemistry*. 26, pp. 1063–1072, XP001040387 (exhibit 32).
International Search Report for PCT/IL 01/00361 (exhibit 33).
International Search Report for PCT/IL 01/00909 (exhibit 34).
Bose et al., *Cell* 82, 405–414 (1995).
Hannun et al., *Biochim. Biophys. Acta* 1154. 223–236 (1993).
Higgins et al., *Trends Biochem. Sci* 17, 18–21 (1992).
Karasavvas et al., *Eur. J. Biochem.* 236, 723–731 (1996).
Nicholson et al., *British J. Cancer* 81, 423–430 (1989).
Suzuki et al., *Exp. Cell Res.* 233, 41–47 (1997).
Wieder et al., *J. Biol. Chem.* 273, 11025–11031 (1998).
Naoya M. et al., (2000) *Analytical Biochemistry* 282, p115–120 XP002212280.

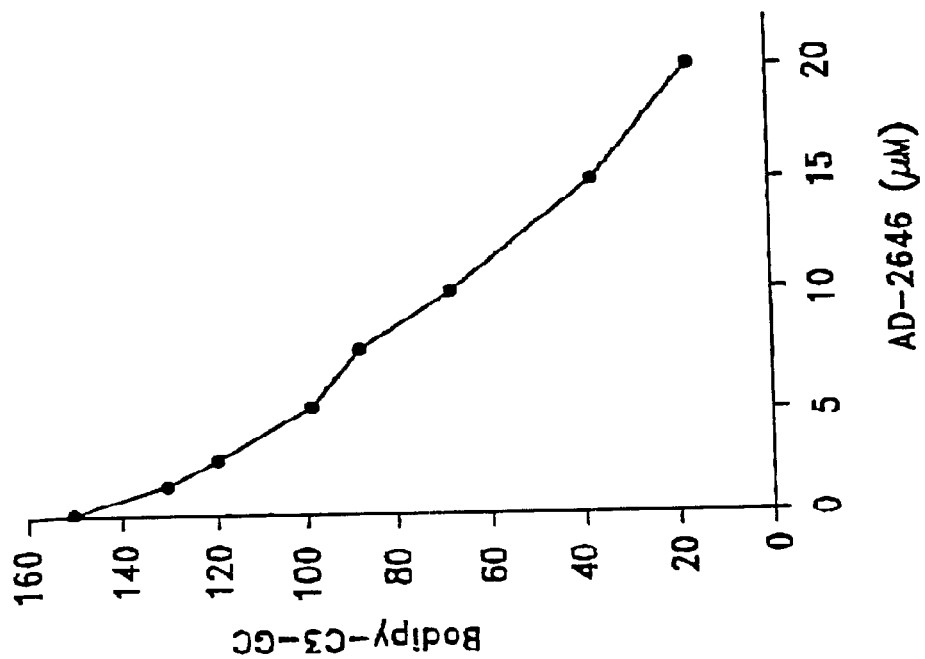
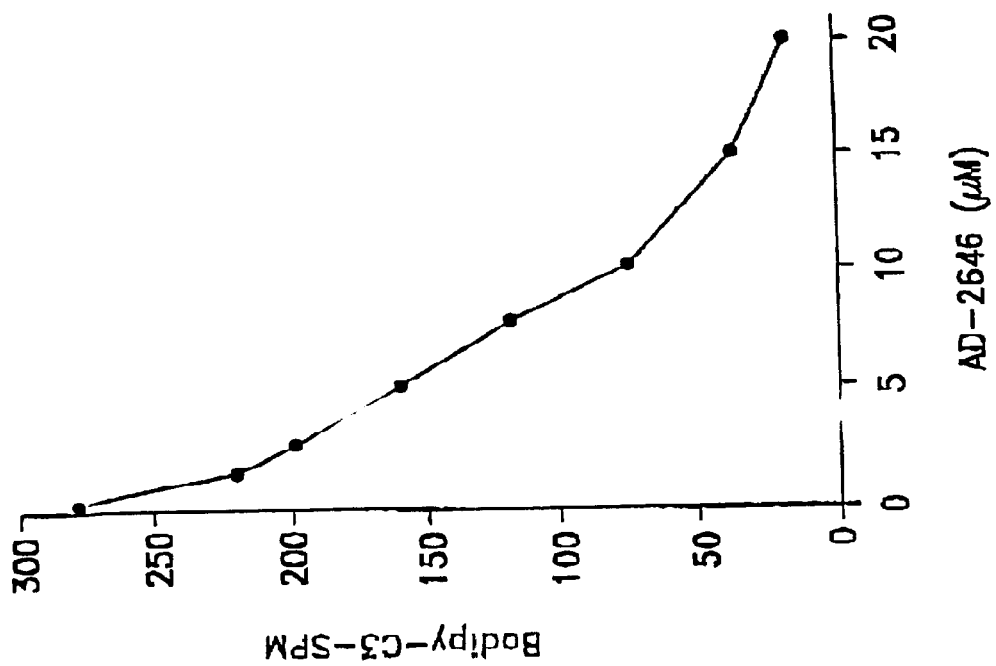

SPHINGOLIPIDS

This application is a continuation of PCT/IL01/00909, filed Sep. 26, 2001, designating the United States of America, and a continuation-in-part of PCT/IL1/00361, filed Apr. 18, 2001, designating the United States of America, which claims benefit of U.S. Provisional Application No. 06/198,513, filed Apr. 19, 2000 the contents of which are hereby incorporated by reference into this application.

BACKGROUND OF THE INVENTION

Sphingolipids (SL) comprise a group of lipids having ceramide, i.e., N-acylsphingosine as the basic group. There are two main types of SL, phosphoSL and glycoSL. While the former have one main component, i.e., sphingomyelin (ceramide-phosphorylcholine), the glycosphingolipids comprise a wide group. They range from monohexosylceramides (ceramide β-glucose and ceramide β-galactose), through oligohexosyl ceramide (e.g., di- and trihexosyl ceramides) to a large number of gangliosides composed of oligohexosyl ceramides to which sialic acid is also linked. SLs are present in practically every cell type and tissue and particularly abound in the nervous system. The relative composition of the SL may change with age; thus, it has been shown that the ratio of sphingomyelin to lecithin increases with age.

Glycosphingolipids have a high binding potential and act as specific receptors for a number of external agents, e.g., lectins, toxins, hormones and viruses. To exemplify: vibrio cholerae toxin links to GMI-ganglioside and Shigella dysenteriae verotoxins to globotriaosyl ceramide.

During the past decade there has been an enormous increase in research on sphingolipids due to discoveries that implicated members of this group in signal transduction processes [recently reviewed in Levade et al., *Biochim. Biophys. Acta* 1438, 1–17 (1999); Mathias et al., *Biochem. J.* 335, 465–480 (1998); Perry et al., *Biochim. Biophys. Acta* 1436, 233–243 (1998); Riboni et al., *Prog. Lipid Res.* 36, 153–195 (1997)]. The most studied compound was ceramide which was shown to play a role in the regulation of key processes such as growth inhibition, differentiation and apoptosis [Hannun et al., *Biochim. Biophys. Acta* 1154, 223–236; Hannun et al., *Trends Cell Biol.* 10, 73–80 (2001); Higgins et al., *Trends Biochem. Sci.* 17, 18–21 (1992)]. SPM is generally considered as the primary metabolic source of ceramide whose generation in a particular location in the cell, (e.g., the membrane) makes it suitable for mediating cellular signaling processes. An increased de novo synthesis of ceramide has also been described as a potential source for signaling [Bose et al., *Cell* 82, 405–414, (1995)]. Therefore, a major effort has been directed to modulate the generation of intracellular ceramide by sphingomyelinases, mostly the neutral, membrane-bound enzyme, although the acidic enzyme has also been implicated. Nevertheless, it should be emphasized that modification of the biosynthetic mechanisms such as reduction of the conversion of ceramide to SPM or glycolipids and, in parallel, its hydrolysis by ceramidases would also increase its concentration in the cell.

The role of sphingolipids in signal transduction [reviewed in L. Riboni et al., *Prog. Lipid Res.* 36, 153–195 (1997) and A. Gomez-Munoz, *Biochim. Biophys. Acta* 1391, 32–109 (1998)] have been extensively studied, and was proposed to operate through the "sphingomyelin cycle". According to this hypothesis, binding a particular extracellular ligand to its receptor activates a plasma membrane-bound sphingomyelinase, giving rise to ceramide, which acts as a mediator of the intracellular effects of the ligand. Numerous publications describe and emphasize the role of ceramide in cell killing by apoptosis as well as its effect on important cellular events such as proliferation, differentiation and reaction to stress conditions. Of particular interest are also reports that short chain, cell-permeable (e.g., $C_2$ or $C_6$) ceramides evoke biological responses that lead to cell killing. Other studies, using the precursor of ceramide, i.e., sphingosine have shown its effects on cell growth and viability. Furthermore, sphingosine was shown to inhibit protein kinase C and increase the intracellular concentration of calcium ions. The phosphorylated form of sphingosine, i.e., sphingosine-1-phosphate has been shown to be a potent activator of phospholipase D. And di- or tri-methylated sphingosine was shown to inhibit growth of cancer cells [Endo et al., *Cancer Research* 51, 1613–1618, (1981)].

The involvement of ceramide and sphingolipid metabolism in cancer has been studied. It have been demonstrated that apoptosis induced by administration of a variety of chemotherapeutic agents is mediated by ceramide [Strum et al., *J. Biol. Chem.* 269, 15493–15497 (1994); Maurer et al., *J. Natl. Cancer Inst.* 91, 1138–1146 (1999); Suzuki et al., *Exp. Cell Res.* 233, 41–47 (1997)]. Anthracyclins (e.g., daunorubicin) have been shown to induce ceramide accumulation which subsequently led to death of cancer cells [Bose et al., *Cell* 82, 405–414 (1995)]. The second line of study showed that drug-resistant cancer cells differ in their sphingolipid metabolism from drug-sensitive ones. Of special interest in this respect are studies of Cabot et al. [Lavie et al., *J. Biol. Chem.* 271, 19530–19536 (1996)], who have demonstrated that glucosylceramide, a direct metabolic product of ceramide, was elevated in several drug-resistant cells overexpressing the P-glycoprotein pump (Pgp). Overexpression of the enzyme that synthesizes this glycolipid, i.e., glucosylceramide synthetase (GCS), by a retroviral expression system resulted in conversion of doxorubicin-sensitive cells into resistant ones [Liu et al., *J. Biol. Chem.* 274, 1140–1146 (1999)]. Conversely, inhibition of GCS expression, by antisense technology, resulted in increased sensitivity to doxorubicin. Cabot et al. have also proposed that drug-resistance modulators such as tamoxifen, verapamil and the cyclosporine analog, PSC 833, exert their effect by inhibition of GCS [Cabot et al., *FEBS Letters* 394, 129–131 (1996), *FEBS Letters* 431, 185–199 (1998); Lavie et al., *J. Biol. Chem.* 272, 1682–1687 (1999); Lucci et al., *Cancer* 86, 300–311 (1999)], resulting in an increase of cellular ceramide. Nicholson et al. (*British J. Cancer* 81, 423–430 (1989)] have shown that an inhibitor of GCS, 1-phenyl-2-decanoyl-amino-3-morpholino-1-propanol, killed preferentially multidrug-resistant cells, compared to their drug-sensitive counterparts. Taken together, the above studies suggest a metabolic mechanism which in MDR-cells decrease their ceramide content by converting it to glucosylceramide, making them resistant to a series of chemotherapeutic drugs.

Of special interest is the mechanism proposed for the anticancer drug hexadecylphosphocholine [HePC, Wieder et al., *J. Biol. Chem.* 273, 11025–11031, (1998)]. This is an antiproliferative drug, which is currently used for the treatment of extraneous metastases of mammary carcinoma and has been shown to induce apoptosis at a concentration of 25 $\mu$M. The above publication provides support that HePC, which inhibits the biosynthesis of phosphatidylcholine exerts a secondary effect by decreasing the biosynthesis of sphingomyelin and consequently increasing the levels of ceramide and it is probably the latter that is responsible for the proapoptotic properties of HePC. And, indeed the authors showed that the PC-induced apoptosis was blocked by Fumonisin B1, an inhibitor of ceramide synthesis. And, short-chain, membrane-permeable ceramides additively increased the apoptotic effect of HePC.

Another major aspect of the metabolism of the sphingolipids is their accumulation in organs of patients afflicted with the genetic lipid storage diseases, such as Gaucher disease (β-glucosidase), Tay-Sachs disease (β-N-acetyl hexosaminidase); Niemann-Pick disease (acid sphingomyelinase), Krabbe disease (β-galactosidase), Metachromatic leukodystrophy (arylsulfatase A), Fabry disease (ceramidase) and Farber disease (α-galactosidase). Each of these diseases is due to a mutation in a gene encoding a lysosomal sphingolipid hydrolase (shown in brackets). Consequently, the activity of the respective hydrolase is considerably reduced resulting in accumulation of the respective sphingolipid in the patients' organs.

Being a metabolic disorder, the metabolic defect and accumulation of the corresponding sphingolipid is a lifelong phenomenon. Three forms of therapy are being used or considered. 1. Enzyme replacement therapy, in which the enzyme involved is purified and infused into the patients for the rest of their lives; this approach is currently applied to patients with Gaucher disease, in which the patients are infused with μ-glucosidase purified from human placentae or, alternatively, a recombinant form of the enzyme. 2. Gene therapy, in which a gene encoding the normal enzyme will be cloned and administered into the patients; this is currently in the stage of planning. 3. Infusion into the patient of an inhibitor of the biosynthesis of the sphingolipid accumulating in the disease, the aim being to reduce the quantity of the sphingolipid accumulating in the patients' organs. This approach is currently in clinical test, on Gaucher disease patients in several medical centers [Cox et al., *The Lancet* 355, 1481–1485, (2000)].

Sphingolipids are of the general structure:

wherein $R_1$ is $CH_3(CH_2)_{14-22}$ and $R_2$ may be a hydrogen atom, phosphoryl-choline; glucose, galactose or an oligosaccharide.

Ceramide, in which $R_2$ is hydrogen, the precursor of the sphingolipids, is a bioeffector molecule, affecting cell differentiation, apoptosis and growth suppression.

Several non-natural analogs of ceramide have been synthesized having a phenyl group instead of the $CH_3(CH_2)_{12}$—CH=CH residue.

For example, the compound PDMP

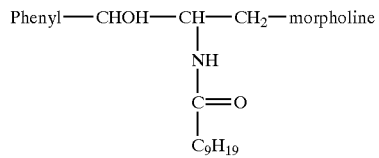

has been shown to be an inhibitor of glucosphingolipid [Vunnam & Radin *Chem. Phys. Lipid* 26, 265 (1980)].

Acyl phenyl amino alcohol (MAPP):

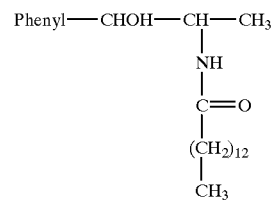

has been shown to inhibit ceramidase, resulting in an inhibition of cell growth [Bielawska et al., *J. Biol. Chem.* 271, 12646–12654 (1996)].

Esters of p-nitrophenyl-amino-propanediol:

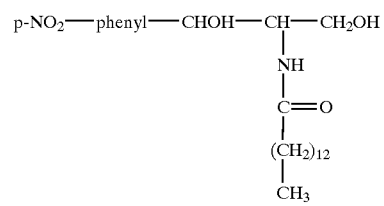

have been shown to inhibit cell differentiation. [Bielawska et al., *J. Biol. Chem.* 267, 18493–18497 (1992)].

Other non-natural derivatives of sphinglipids affect cell growth and differentiation. For example N,N,N-trimethyl sphingosine has been shown to inhibit cell growth [Endo et al., *Cancer Research*, 51, 1613–1618 (1991)]. $C_8$ ceramide in which the amide group was replaced by —NH—$(CH_2)_7CH_3$: $CH_3(CH_2)_{12}$—CH=CH—CHOH—CHNH[$(CH_2)_7CH_3$]—$CH_2OH$ induced apoptosis [Karasavvas et al., *Eur. J Biochem.* 236, 729–731 (1996)].

Hexadecylphosphocholine induced a ceramide-mediated apoptosis [Wieder et al., *J. Biol. Chem.* 273, 11025–11031 (1998)].

It is an object of the present invention to provide novel therapeutic compounds that can modify the metabolism of sphingolipids.

It is a further object of this invention to provide novel therapeutic compounds that may be used for killing of unwanted cells.

These and other objects of the invention will become clearer as the description proceeds.

SUMMARY OF THE INVENTION

The invention relates to compounds of the general formula (1):

(I)

wherein
R represent a linear or branched, saturated, or unsaturated alkyl or alkenyl chain, which may optionally be substituted by hydroxyl, $CH_3(CH_2)_m CH=CH$—, $CH_3(CH_2)_m$, wherein m is zero or an integer of from 1 to 20, phenyl, optionally substituted by nitro, amino, alkylamino, acylamino, —NHC(S)NH-alkyl, sulfonylamido-alkyl, a group

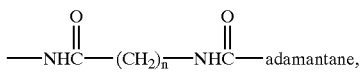

wherein n is an integer of from 1 to 20, or a group —NH-adamantane, —NH-t-BOC, —NH-FMOC or NH-CBZ;

X represents hydrogen or the group —$OR_4$ in which $R_4$ is hydrogen or a linear or branched, saturated or unsaturated $C_1$–$C_6$ alkyl or alkenyl chain which may be optionally substituted with hydroxy;

Y represents —$NH_2$, $NHR^x$ wherein $R^x$ is hydrogen, a linear or branched alkyl or alkenyl chain which may be optionally substituted with hydroxy, an amino protecting group,

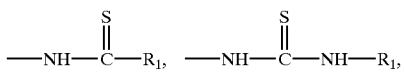

—$NH(SO_2)R_1$, —$NR_1R_2$, —$N^+R_1R_2R_3$, wherein $R_1$, $R_2$ and $R_3$, which may be identical or different each represent $C_{1-6}$alkyl or $C_{1-6}$alkenyl, a group

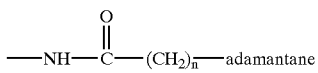

wherein n is zero or an integer of from 1 to 20, a group —NH-adamantane, a group

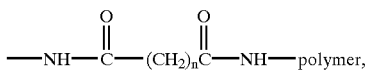

where "polymer" designates a natural or synthetic biocompatible polymer having a molecular weight between $10^3$ and $10^6$ daltons;

Z represents hydrogen, —OH, a mono- or disaccharide, a monosaccharide sulfate and choline phosphate;

with the proviso that

Y cannot represent $NH_2$ when R represents an alkyl, the group $CH_3(CH_2)_m CH=CH$—, phenyl or nitro phenyl; and Y cannot represent the groups —$NR_1R_2$ or —$N^+R_1R_2R_3$, or $NHR_4$ where $R_4$ represents octyl when $R_1$ represents a methyl, R represents the group $CH_3(CH_2)_m CH=CH$— and Z represents —OH;

and isomers and pharmaceutically acceptable salts thereof.

The invention also relates to a pharmaceutical composition comprising as active ingredient a compound of formula (I) wherein the substituents are as defined in claim 1, and optionally further comprising pharmaceutically acceptable carrier, adjuvant or diluent.

The pharmaceutical compositions of the invention may be used for reducing accumulation of sphinglipids, and thus for the treatment of lipid storage diseases such as Gaucher disease, Tay-Sachs disease, Niemann-Pick disease, Krabbe disease, Metachromatic leukodystrophy, Fabry disease and Farber disease.

The novel compounds of formula (I) may be used as inhibitors of acidic, neutral and alkaline sphingomyelinases, acidic, neutral and alkaline ceramidases, α-galactosyl synthetase, ceramide synthetase, sphingomyelin synthetase and glycoceramides synthetase.

The pharmaceutical compositions of the invention may also be used for the treatment of cancerous diseases, for killing of wild type and drug-resistant cancer cells.

The pharmaceutical compositions of the invention may also be used for the treatment of parasitic, viral, bacterial, fungal and prion diseases.

In a further aspect the invention relates to a method of treating a lipid storage disease or a cancerous disease in a patient in need of such treatment comprising administering to said patient a therapeutically effective amount of a compound of formula (I) or of pharmaceutical composition comprising the same.

HL60 cell viability was tested in the presence of increasing concentrations of AD-2646. Abbreviations: Via (viable), C (cells), Contr (control), Inhi (inhibitor), Conc (concentration).

Figure 2:
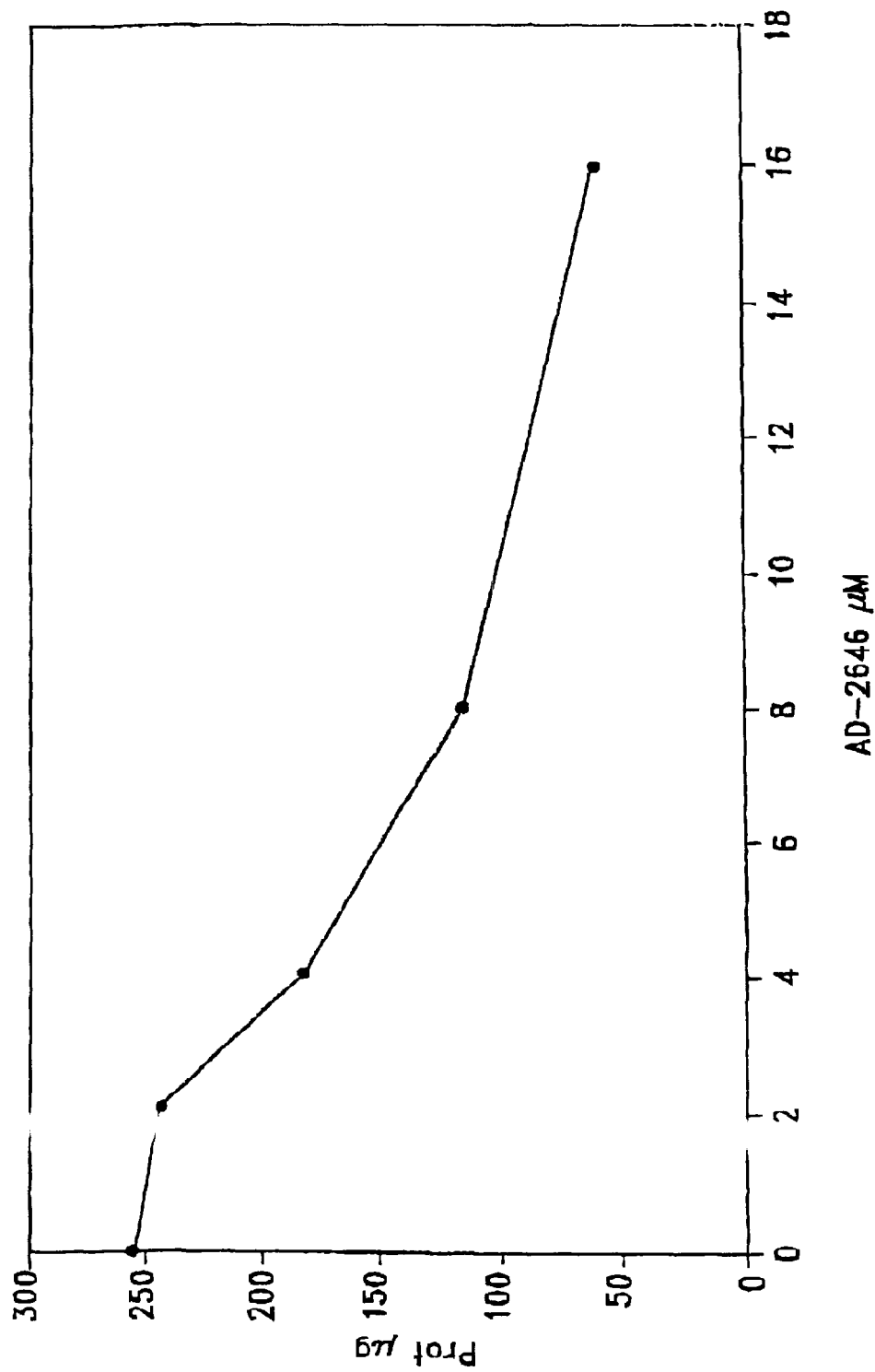

FIG. 2—AD-2646 cytotoxic effect on TSU-PR1 cells

The cytotoxic effect of AD-2646 was examined using increasing concentrations of AD-2646 for two days. The total protein content was measured. Abbreviations: Prot (protein).

FIG. 3—Effect of AD-2646 on sphingolipids metabolism (SPM)

HL60 cells were incubated with increasing concentrations of AD-2646 for 3 hours in the presence of 2.5 μM Bodipy-C3-ceramide. After extraction, the lipids were applied onto a thin layer chromatography plate, and the fluorescence of Bodipy-C3-sphingomyelin (SPM) was quantified.

FIG. 4—Effect of AD-2646 on sphingolipids metabolism (GC)

HL60 cells were incubated with increasing concentrations of AD-2646 for 3 hours in the presence of 2.5 μM Bodipy-C3-ceramide. After extraction, the lipids were applied on a thin layer chromatography plate, and the fluorescence of Bodipy-C3-cerebi-oside (GC) was quantified.

Figure 5:
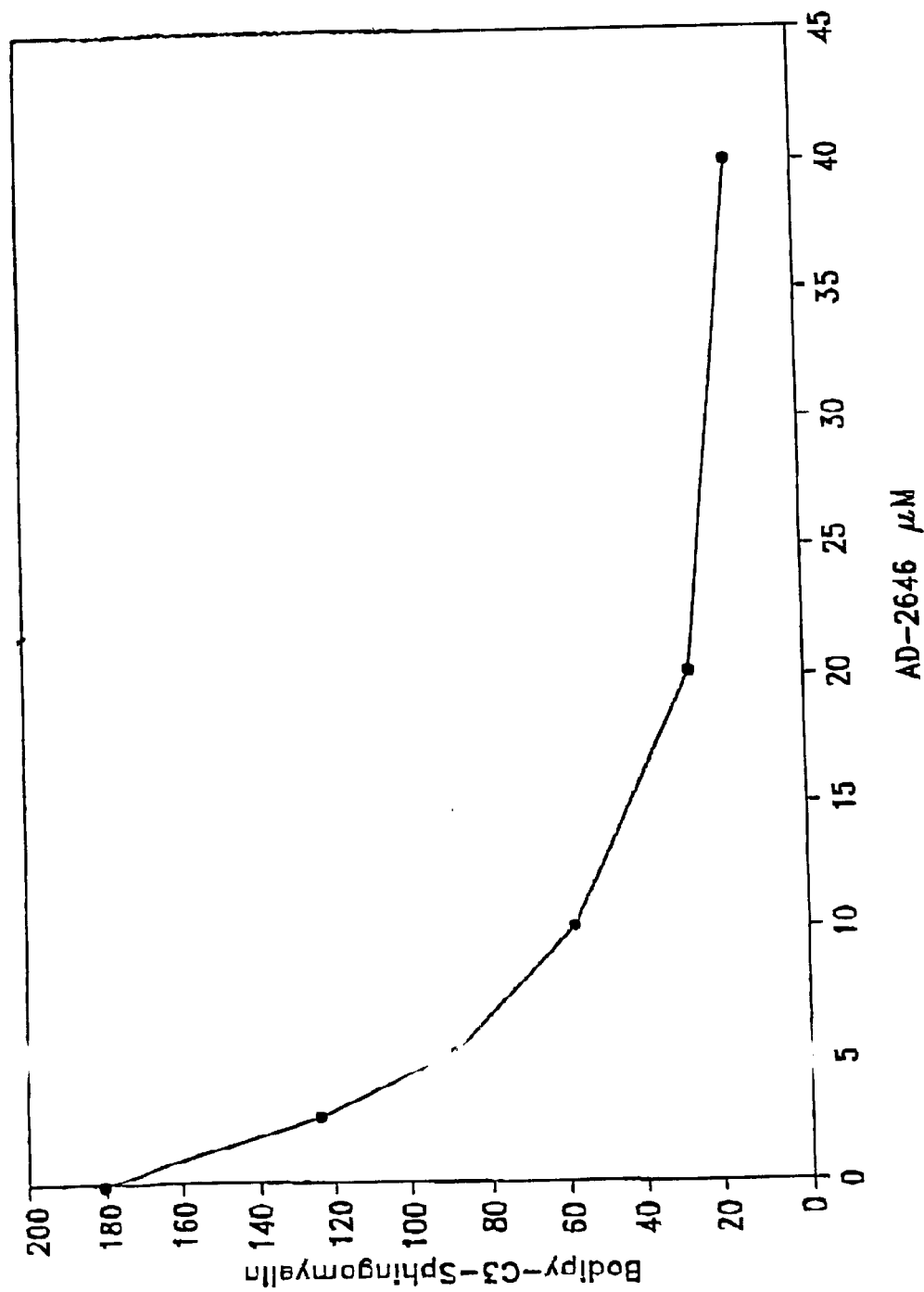

FIG. 5—AD-2646 inhibits SPM synthesis in TSU-PR1 cells

TSU-PR1 cells were incubated for 3 hours in the presence of increasing concentrations of AD-2646 and the fluorescence of Bodipy-C3-sphingomyelin (SPM) was quantified.

Figure 6:
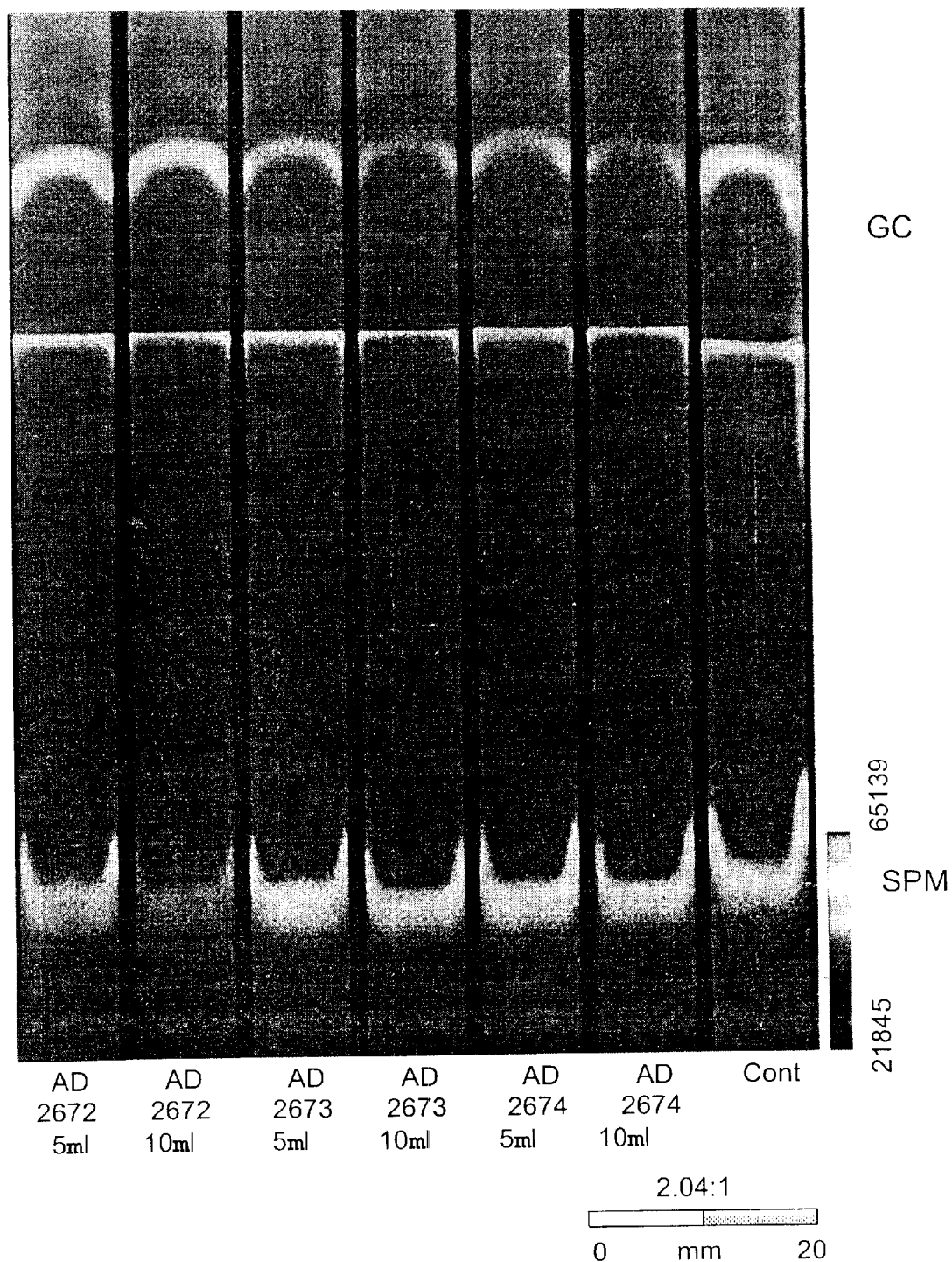

FIG. 6—Inhibition of sphingolipids metabolism by the compounds of the invention

HL60 cells were incubated with the different compounds AD-2672, AD-2673 and AD-2674, each at 5 and 10 μM. The effect of the different compounds on synthesis of Bod3-SPM and Bod3-GC was examined. The relative quantity of the SPM and GC is shown in the fluorescent image of the plate Abbreiations: Cont (control).

DETAILED DESCRIPTION OF THE INVENTION

In search for substances that could modify the metabolism of sphingolipids, the inventors have synthesized a range of new compounds, having the general formula (I):

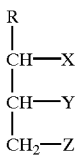 (I)

Wherein
R represent a linear or branched, saturated, or unsaturated alkyl or alkenyl chain, which may optionally be substituted by hydroxyl, $CH_3(CH_2)_m CH=CH-$, $CH_3(CH_2)_m$, wherein m is zero or an integer of from 1 to 20, phenyl, optionally substituted by nitro, amino, alkylamino, acylamino, —NHC(S)NH-alkyl, sulfonylamidoalkyl, a group

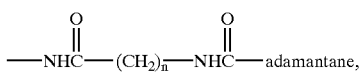

wherein n is an integer of from 1 to 20, NH-adamantane, or a group —NH-t-BOC, —NH-FMOC, or NH-CBZ;

X represents hydrogen or the group —$OR_4$ in which $R_4$ is hydrogen or a linear or branched, saturated or unsaturated $C_1$–$C_6$ alkyl or alkenyl chain which may be optionally substituted with hydroxy;

Y represents —$NH_2$, $NHR^x$ wherein $R^x$ is hydrogen, a linear or branched alkyl or alkenyl chain which may be optionally substituted with hydroxy, an amino protecting group,

—$NH(SO_2)R_1$, —$NR_1R_2$, —$N^+R_1R_2R_3$, wherein $R_1$, $R_2$ and $R_3$, which may be identical or different each represent $C_{1-6}$alkyl or $C_{1-6}$alkenyl, a group

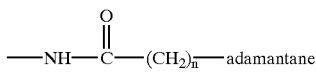

wherein n is zero or an integer of from 1 to 20, a group —NH-adamantane, a group

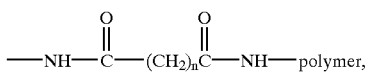

where "polymer" designates a natural or synthetic biocompatible polymer having a molecular weight between $10^3$ and $10^6$ daltons;

Z represents hydrogen, —OH, a mono- or disaccharide, a monosaccharide sulfate and choline phosphate;
with the proviso that
Y cannot represent $NH_2$ when R represents an alkyl or alkenyl chain, the group $CH_3(CH_2)_m CH=CH-$, phenyl or nitro phenyl; and
Y cannot represent the groups —$NR_1R_2$ or —$N^+R^1R_2R_3$, or $NHR4$ where $R_4$ represents octyl when $R_1$ represents methyl, R represents the group $CH_3(CH_2)_m CH=CH-$ and Z represents —OH;

and isomers and pharmaceutically acceptable salts thereof.

Preferred compounds of formula (I) are those in which R designates aminophenyl or nitrophenyl.

Also preferred are compounds of formula (I) in which Y represents —$NH_2$ or —$NHR^x$, particularly compounds in which $R^x$ designates an alkyl chain.

The amino protecting groups may be any suitable amino protecting groups as known to the man of skill in the art, particularly BOC (tertiary, butyloxy carbonyl), FMOC (fluorenylmethoxycarbonyl) or CBZ (benzyloxycarbonyl).

Some specific particularly preferred compounds are listed hereunder. It is to be noted that the length of the alkyl or alkenyl chains may be varied. Compounds containing an adamantyl moiety may be advantageous, as due to the size and configuration of this group the compound may be arrested in the cell membrane, and influence enzymes within this membrane.

Other preferred compounds may be those in which Y represents a group (designated AD-2665)

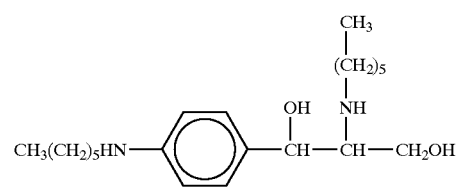

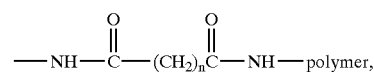

where "polymer" designates a natural or synthetic biocompatible polymer having a molecular weight of $10^3$–$10^6$, like heparin, hyaluronic acid, dextran, (designated AD-2687)

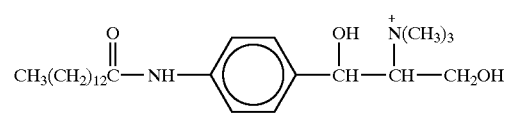

carboxymethylcellulose, chondroitin sulfate, dermatan sulfate, polyethyleneglycol, peptides or proteins. Such polymeric compounds of the invention are unable to penetrate the cell membrane and enter the cells, and will thus enable inhibition only at the outer cell membrane or extracellular surroundings.

(designated AD-2646)

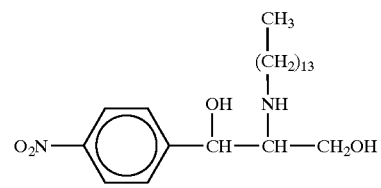

Some specific preferred compounds are the following:

(designated AD-2672)

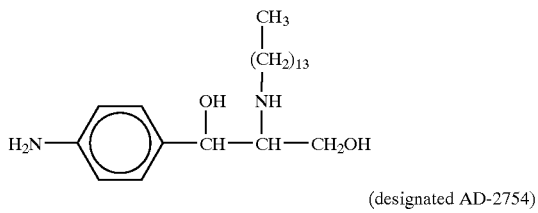

(designated AD-2754)

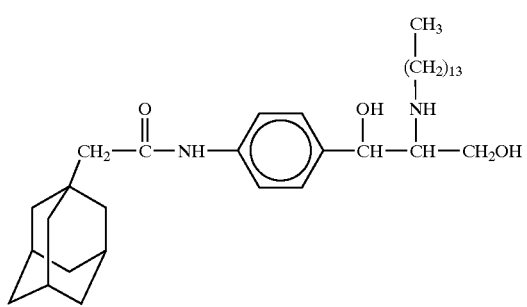

(designated AD-2673)

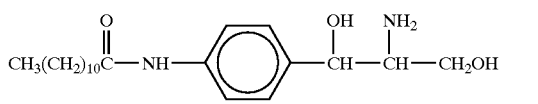

(designated AD-2144)

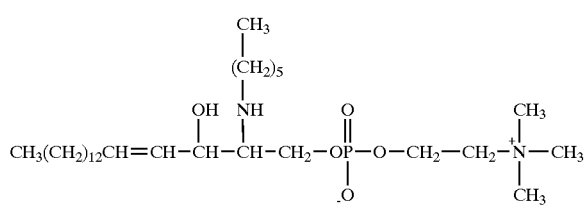

As shown in the following Examples, the novel synthetic compounds of the invention are capable of inhibiting degradation as well as biosynthesis of sphingolipids. As such, these compounds may be used in the treatment of lipidoses, particularly genetic lipid storage diseases in which sphingolipids accumulate in organs of afflicted patients, such as Gaucher disease, Tay-Sachs disease, Niemann-Pick disease, Krabbe disease, Metachromatic leukodystrophy, Fabry disease and Farber disease. Pharmaceutical compositions for the treatment of lipid storage diseases are also within scope of the present invention.

Use of the compounds of the invention has also resulted in killing of a variety of cells, including drug-sensitive and drug-resistant cells, alone or in combination with other anti-cancer drugs. The invention thus also relates to pharmaceutical compositions for the treatment of cancerous diseases, comprising as active ingredients the compounds of the invention, optionally in combination with at least one other anti-cancer drug.

Still further, the compounds of the invention may be used in the treatment of parasitic diseases such as malaria and leishmania. Pharmaceutical compositions for the treatment of such parasitic diseases are also within scope of the present invention.

The compounds of the invention are generally provided in the form of pharmaceutical compositions. Said compositions are for use by injection or by oral uptake.

The pharmaceutical compositions of the invention generally comprise a buffering agent, an agent which adjusts the osmolarity thereof, and optionally, one or more carriers, excipients and/or additives as known in the art, e.g., for the purposes of adding flavors, colors, lubrication, or the like to the pharmaceutical composition.

Each carrier should be both pharmaceutically and physiologically acceptable in the sense of being compatible with the other ingredients and not injurious to the subject to be treated. While formulations include those suitable for rectal, nasal, preferred formulations are intended for oral or parenteral administration, including intramuscular, intradermal, subcutaneous and specifically intravenous administration. The formulations may conveniently be presented in unit dosage form and may be prepared by any methods known in the art of pharmacy.

Carriers may include starch and derivatives thereof, cellulose and derivatives thereof, e.g., microcrystalline cellulose, xantham gum, and the like. Lubricants may include hydrogenated castor oil and the like.

A preferred buffering agent is phosphate-buffered saline solution (PBS), which solution is also adjusted for osmolarity.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

A preferred pharmaceutical formulation is preferably used for administration by injection, including intravenous injection.

The compositions of the invention may be administered in a variety of ways. By way of non-limiting example, the composition may be delivered by injection intravenously, intramuscularly, or intraperitoneally. Intravenous administration, for example, is advantageous.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

For oral administration, the composition of the invention may be mixed with nutritive feed material or water supplies for the subject to be treated. It is contemplated however that the effective composition can either be mixed with the nutritive feed material or water or fed to the subject separately.

The preparation of pharmaceutical compositions is well known in the art and has been described in many articles and textbooks, see e.g., Remington's Pharmaceutiçahiences, Gennaro A. R. ed., Mack Publishing Company, Easton, Pa., 1990, and especially pages 1521–1712 therein.

Additives may also be designed to enhance uptake of the active agent across cell membranes. Such agents are generally agents that will enhance cellular uptake of the molecules of the invention. For example, the compounds of the invention may be enclosed within liposomes. The preparation and use of liposomes, e.g., using particular transfection reagents, is well known in the art. Other methods of obtaining liposomes include the use of Sendai virus or of other viruses.

The above-mentioned lipid agents may also improve the stability of the active compounds that have been taken up by the cell.

The dose of the active agent may vary. The dose would generally depend on the disease, the state of the disease, age, weight and sex of the patient, and is to be determined by the attending physician.

The invention also relates to a method for the treatment or prevention of a lipid storage disease, a cancerous disease or a parasitic disease, comprising administering a compound or a pharmaceutical composition of the invention or of any of the preferred embodiments thereof, to a patient in need thereof.

A number of methods of the art of molecular biology are not detailed herein, as they are well known to the person of skill in the art. Such methods include site-directed mutagenesis, PCR cloning, expression of cDNAs, analysis of recombinant proteins or peptides, transformation of bacterial and yeast cells, transfection of mammalian cells, and the like. Textbooks describing such methods are e.g., Sambrook et al., Molecular Cloning A Laboratory Manual, Cold Spring Harbor Laboratory; ISBN: 0879693096, 1989, Current Protocols in Molecular Biology, by F. M. Ausubel, ISBN: 047150338X, John Wiley & Sons, Inc. 1988, and Short Protocols in Molecular Biology, by F. M. Ausubel et al. (eds.)₃rd ed. John Wiley & Sons; ISBN: 0471137812, 1995. These publications are incorporated herein in their entirety by reference. Furthermore, a number of immunological techniques are not in each instance described herein in detail, as they are well known to the person of skill in the art. See e.g., Current Protocols in Immunology, Coligan et al. (eds), John Wiley & Sons. Inc., New York, N.Y.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It must be noted that, as used in this specification and the appended claims, the singular forms "a", "an" and "the" include plural referents unless the content clearly dictates otherwise.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

The following examples are thus only representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Cell Lines

HL60: Human leukemia cell line (ATCC CCL-240).

TSU-PR1: Prostate cancer cells (available at the ATCC).

rR: Human breast cancer cells, drug resistant (available at the ATCC).

MCF7-NCi: Human breast cancer cells, drug sensitive (available at the ATCC).

U937: Myeloid Leukemic cells (available at the ATCC).

Example 1

Synthesis of Compounds

1. Preparation of (2R,3R)-2-(N-hexylamine)-1-(4-nitrophenyl)-1,3-propanediol (AD-2593)

2 gr (2R,3R)-2-amino-T-(4-nitrophenyl)-1,3-propanediol were dissolved in 50 ml methanol in a round bottom flask. To the magnetically-stirred solution were added 5 ml of 0.1 N HCl, followed by 2 gr of hexylaldehyde (hexanal). The mixture was stirred for 30 min, after which 1 gr of $NaBH_4$ was added in several portions during 3 hours. The mixture was left to stir overnight, the solution was transferred to a separatory funnel, 100 ml of $H_2O$ and 100 ml dichloromethane were added and the solvent mixture was shaken. The lower phase was collected, the aqueous-methanol phase was extracted twice with 50 ml 3:1 dichloromethane:methanol, the 3 lower phases were combined and shaken with 75 ml $H_2O$. The organic phase was dried with $MgSO_4$, filtered and evaporated to dryness. The residue was dissolved in a small volume of dichloromethane: methanol, 1:1, and loaded onto a 50×2 cm silica gel column. The compound was eluted with dichloromethane containing increased amounts of methanol. Yield: 1.2 gr; M.S. $I^+$=296.

2. Preparation of (2S,3R) 2-amino-1-(4-aminophenyl)-1,3-propanediol (AD-2516)

5 gr (2S,3R)-2-amino-1-(4-aminophenyl)-1,3-propanediol were dissolved in 150 ml methanol, 100 mg 10% Pd/C were added and the solution was hydrogenated for 6 h at 50 Psi in a hydrogenator at room temperature. The catalyst was removed by filtration and the solution was evaporated to dryness. The dry compound was used for synthesis without further purification. Yield: 5 gr; M.S. $I^+$=183.

3. Preparation of (2S,3S)-2-(N-octylamine)-1-(4-N-octylaminophenyl)-1,3-propanediol (AD-2670)

3 gr (2S,3S)-2-amino-1-(4-aminophenyl)-1,3-propanediol (prepared as in AD-2516) were dissolved in 100 ml methanol:water 1:1 in a round bottom flask. The solution was magnetically stirred and 1 ml octyl aldehyde (octanal) was added followed by 1 ml acetic acid. The solution was stirred for 15 min and 1 gr of sodium cyanoborohydride NaCNBH$_3$ was added in portions during 2 hours. The solution was stirred for another 3 h, then transferred to a separatory funnel and 100 ml water, and 50 ml dichloromethane and 25 ml methanol were added. Following shaking, the lower phase was collected and the upper, aqueous-methanolic phase was extracted twice with 50 ml CH$_2$Cl$_2$:MeOH, 3:1. The combined organic phases were washed with 100 ml H$_2$O, dried for 2 hours over MgSO$_4$, filtered and the solution was evaporated to dryness. The residue was dissolved in minimal amount of dichloromethane methanol, 1:1, and loaded onto a 2×50 cm silica gel. The column was eluted with increasing amounts of methanol in dichloromethane. Yield: 2.1 gr; M.S. I$^+$=407.

4. Preparation of (2R,3R)-2-BOC amino-1-(4-nitrophenyl)-1,3-propanediol (AD-2502)

8 gr (2R,3R)-2-amino-1-(4-nitrophenyl)-1,3-propanediol were dissolved in 100 ml dichloromethane methanol, 2:1, and 6 gr of BOC anhydride, dissolved in 50 ml of the same solvent mixture were added. The solution was introduced into 250 ml Erlenmeyer and stirred for 30 min, when it became clear. Then left to stir for another 12 h. The solution was evaporated to dryness and the residue was dissolved in 100 ml water and 80 ml isopropanol, then transferred into a separatory funnel and washed with 100 ml heptane. The heptane phase was removed and another amount of 60 ml heptane was added. The phases were mixed and the heptane phase removed. The water phase was extracted with 100 ml dichloromethane. The dichloromethane phase was dried oil 5 gr MgSO$_4$ during 2 hours, then filtered and evaporated to dryness. The compound was used without further purification; Yield: 8 gr; M.S. I$^+$=313.

5. Preparation of (2R,3S)-2-BOC-amino-1-(4-N-hexadecanoyl-aminophenyl)-647 1,3-propanediol (AD-2522)

BOC was linked to 4 gr 2R, 3S-2-amino-1-(4-nitrophenyl)-1,3-propanediol as in the preparation of AD2502 (4). 2 grams of the BOC derivative were reduced by hydrogen as in AD2516 (2). 1 gr of the product, i.e., the respective amino phenyl derivative, was reacted with 1 gr hexadecanoic acid in 50 ml dichloromethane:methanol, 2:1, by addition of 1 gr EDAC. The reaction mixture was stirred overnight, evaporated to dryness, the residue was dissolved in 4 ml dichloromethane-methanol, 1:1 and loaded onto a 50×1.5 cm silica gel column prepared in dichloromethane. The compound was eluted with mixtures of dichloromethane and increasing amounts of methanol. Overall yield: 4.5 gr; M.S. I$^+$=521.

6. Preparation of (2R,3R)-2-amino-1-(4-N-butyroylaminophenyl-1,3-propanediol (AD-2602)

2 gr of (2R,3R)-2-BOC-amino-1-(4-N-butyroylaminophenyl)-1,3-propanediol (prepared as in the preparation of compound AD-2522, using butyric acid instead of hexadecanoic acid), were dissolved in 10 ml trifluoroacetic acid (TFA):dichloromethane, 1:1. The mixture was transferred to a 20 ml screw-capped test tube and kept for 2 h at 37° C. with occasional stirring, then evaporated to dryness in a ratavapor and the residue purified using a silica gel column eluted with dichloromethane and increasing amounts of methanol. Yield: 1.2 gr; M.S. I$^+$=353.

7. Preparation of 2-N,N,N-trimethylamino-1-(4-N-dodecanoyl-aminophenyl)-3-propanol (AD-2687)

2 gr of 2-amino-1-(4-N-dodecanoylamino phenyl)-3-propanol was prepared as in the preparation of AD-2602 (6) from the corresponding starting material. The compound was dissolved in 20 ml of methanol in a screw-capped pressure glass tube. 4 ml CH$_3$J were added followed by 1 gr of sodium carbonate. The pressure glass tube was sealed and immersed in a heating bath at 80° C. for 12 h. The tube was cooled and opened. The solution was transferred to a round bottom flask and evaporated to dryness. The residue was dissolved in a minimal amount of dichloromethane:methanol, 1:1, loaded onto a silica gel column and eluted with solutions of dichloromethane and increasing methanol. Yield: 1.6 gr; M.S. I$^+$=408.

8. Preparation of Sphingosyl-N-Butyl Sulfonamide (AD-2208-B)

200 mg of sphingosine were dissolved in 10 ml dichloromethane:methanol, 2:1, in a 25 ml Erlenmeyer flask. 200 µl of butylsulfonylchloride were added and the solution was stirred for 10 min. 300 µl of triethylamine were then added in 50 µl portions during 1 h and the solution was stirred overnight. The solution was transferred to a 250 ml separatory funnel, a mixture of 50 ml dichloromethane, 15 ml methanol and 25 ml water were added and the solution was shaken in the separatory funnel. The organic phase was washed with 25 ml of 0.1 N HCl, then with water, and dried over MgSO$_4$. It was filtered, evaporated to dryness, the residue was dissolved in 1 ml dichloromethane-methanol and loaded onto a small silica gel column. The product was eluted with increasing ratios of methanol in dichloromethane. Yield: 150 mg; M.S. main I$^+$=420.

9. Preparation of Sphingosylphosphorylcholine-N-Ethyl Thiourea (AD-2209)

100 mg of sphingosylphosphorylcholine were dissolved in 10 ml methanol:water, 2:1, in a 25 ml Erlenmeyer flask. To the stirred solution were added 100 mg of tertiary butyl isothiocyanate. The solution was stirred for 10 min, then 2.5 ml of 1N sodium bicarbonate were added. The solution was left to stir for 48 hours, transferred to a separatory funnel and 80 ml dichloromethane, 30 ml methanol and 40 ml water were added. The organic phase was washed with 40 ml of water, then dried over MgSO$_4$, filtered and evaporated to dryness. The compound was purified by preparative TLC using dichloromethane:methanol:water, 65:35:5 for development. The silica spot containing the product was viewed by an ultraviolet lamp, scraped and eluted with dichloromethane: methanol:water, 1:2:1, in a small column. Yield: 80 mg; M.S. Na$^+$=574.

10. Preparation of L-Erythro Sphingosyl-N-Dodecyl (AD-2754)

100 mg of synthetic L-erythro sphingosine was dissolved in 30 ml methanol in a 50 ml round bottom flask, equipped with a magnetic stirrer and a reflux condenser. 200 mg dodecyl bromide were added, followed by 300 mg sodium carbonate. The flask (was heated in a water bath and the solution refluxed for 24 hours. The solution was transferred to a 250 ml separatory funnel, 50 ml dichloromethane and 30 ml water were added and the lower, organic phase was collected and washed with 25 ml of 0.5N HCl and then twice with 25 ml water: The organic phase was dried over 2 gr of MgSO$_4$, filtered and evaporated to dryness. The residue was dissolved in 1 ml dichloromethane: methanol, 1:1, loaded onto a small silica gel column and the product eluted with increasing ratios of methanol and dichloromethane. Yield: 70 mg; M.S. I$^+$=468.

11. L-Erythro Sphingosyl Phosphorylcholine-N-Hexyl (AD-2144)

100 mg of sphingosyl phosphoryl choline were dissolved in 25 ml methanol:water 1:1 in 100 ml Erlenmeyer flask. The solution was stirred on a magentic stirrer and 100 mg hexanal and 250 µl acetic acid were added. The mixture was stirred for 20 min and 100 mg NaCNBH$_3$ was added. After overnight stirring at room temperature the solvents were evaporated to dryness and the residue was washed and purified as was done in preparation of AD-2209 (9). Yield: 65 mg; M.S. Na$^+$=562.

12. D,L-1,3-dihydroxy-2-[amino(N-FMOCpropyl-3-amine)]-octadecane (AD-2751)

300 mg of DL-1,3-dihydroxy-2-aminooctadecane were dissolved in 50 ml methanol:water 1:1. 100 mg FMOC β-alaninal (N-FMOC 3 aminopropanal) were added followed by 0.5 ml acetic acid. The solution was stirred during 20 min and 200 mg NaCNBH$_3$ were added in portions during 1 hour. The mixture was left to stir for 5 hours, evaporated to dryness, redissolved in a minimal amount of dichloromethane: methanol, 2:1, and purified by column chromatography on a silica gel column and with increasing ratios of methanol and dichloromethane. Yield: 200 mg; M.S. I$^+$=581.

13. D,L-1,3-dihydroxy-2-[amino(3-aminopropyl)]-octadecane (AD-2752)

50 mg D,L-1,3-dihydroxy-2-[amino(N-FMOC propyl-3-amine)] octadecane were dissolved in 4 ml methanol and 1 ml piperidine. The mixture was stirred for 30 min, then evaporated to dryness under a nitrogen stream. The product was purified using a preparative thin layer chromatography silica plate developed with a solution of dichloromethane:methanol:ammonium:hydroxide:water, 80:20:1:1. The product (viewed with a UV-lamp) was scraped and eluted from the silica gel in a small column using dichloromethane:methanol:water, 1:2:1. Yield 30 mg M.S. I$^+$=359.

14. (2R,3S)-2-BOC-amino-1-[4-N-(dodecanoyl-12-N-BOC amine)-phenyl)-1,3-propanediol (AD-2620)

BOC was linked to 3 gr (2R,3S)-2-amino-1-(4-nitrophenyl)-1,3-propanediol as was done in the preparation of AD-2502 (4). Three grams of the BOC derivative were reduced by hydrogen as in the preparation of AD-2516 (2). Two grams of the product were reacted with 1 gr BOC 12 aminododecanoic acid in 50 ml dichloromethane:methanol 2:1 by addition of 500 mg EDAC. The mixture was stirred overnight, evaporated to dryness and purified as in the preparation of AD-2687 (7). Overall yield: 2.5 gr; M.S. I$^+$=673.

15. (2R,3R)-2-amino-1-(4-amino phenyl)-], 3-propanediol (A D-2516B)

This compound was prepared by hydrogenation of 5 gr of (2R,3R)-2-amino-1-(4-nitrophenyl)-1,3-propanediol as was done in preparation of AD-2516 (2). Yield: 4.9 gr; M.S. I$^+$=183.

16. (2R,3R)-2-(N-hexylamine)-1-(4-N-hexylaminophenyl)-1,3-propanediol (AD-2665)

1 gr of (2R,3R)-2-amino-1-(4-aminophenyl)-1,3-propanediol was reacted with 2 gr of hexanal as was done in the preparation of AD-2593 (1) and purified in a similar procedure. The compound was quantified in a spectrophotometer providing a peak at 255 nm and a molar extinction coefficient of 16.6 optical density units per µmole per ml. Yield: 800 mg; M.S. I$^+$=351.

17. (2R,3R)-2-(N-tetradecylamine)-1-(4-nitrophenyl)-1,3-propanediol (AD-2646)

3 gr of (2R,3R)-2 amino-1-(4-nitrophenyl)-1,3-propanediol were dissolved in 100 ml ethanol, 4 ml tetradecyl bromide were added followed by 5 ml diisopropyl ethylamine. The mixture was heated to reflux during 24 h in a 250 ml round bottom flask equipped with a reflux condenser and stirred on a magnetic stirrer. The solution was evaporated to dryness and dissolved in 200 ml dichloromethane methanol, 2:1, transferred to a 500 ml separatory funnel and washed with 75 ml 0.2N HCl. Phases were separated and the organic phase was washed again with 75 ml 0.1N HCl and 15 ml methanol. The organic phase was separated and dried on 5 gr magnesium sulfate, filtered and evaporated to dryness. The resulting oil was dissolved in minimal amount of warm ether and left to crystallize overnight at −20° C. Crystals were filtered at low temperature and recrystallized from hot ether containing 3% of H$_2$O. Yield, 3.6 gr. This compound was quantified in a spectrophotometer providing a peak at 270 nm. Its molar extinction coefficient was 7.84 optical density units per micromole per ml. M.S. I$^+$=409.

NMR: (CDCl$_3$) 0.88, t(3H); 1.26, m (22H); 1.48, m (2H); 2.54, m (1H); 2.73, m (2H); 3.30, broad s (3H); 7.6, d (2H); 8.2, d (2H).

18. (2R,3R)-2-(N-tetradecylamine)-1-(4-aminophenyl)-1,3-propanediol (AD-2672)

2 gr of (2R,3R)-2-(N-tetradecyl amine)-1-(4-nitrophenyl)-1,3-propanediol (AD-2644) were hydrogenated as was done in the preparation of AD-2516 (2). The resulting oil was purified by column chromatography on silica gel eluted with increasing concentrations of methanol in dichloromethane. Yield: 1.5 gr; M.S. I$^+$=378.

19. (2R,3R)-2 amino-1-(N-dodecanoylaminophenyl)-1,3-propanediol (AD-2673)

This compound was prepared from 2 gr of (2R,3R)-2(N-tBOC amino)-1-(N-dodecanoylaminophenyl)-1,3-propanediol (AD-2582) using the same protocol as in the preparation of AD-2602 (6). Overall Yield: 1.3 gr M.S. I$^+$=365.

20. The 2S,3S counterpart was prepared by the same procedure and named AD-2674.

21. (2R,3R)-2-(N,N,N-trimethylamine)-1-(N-tetradecanoyl-4-amino phenyl)-1,3-propanediol (AD-2687)

This compound was prepared from 2 gr (2R,3R)-2-(N,N,N-trimethyl amine)-1-(4-aminophenyl)-1,3-propanediol (AD 2671) prepared as in the preparation of AD-2516 (2) from 3 gr of (2R,3R)-2-(N,N,N-trimethylamine)-1-(4-nitrophenyl)-1,3-propanediol (AD-2667) prepared as in the preparation of AD-2687 (7) from 5 gr (2R,3R)-2-amino-1-(4-nitrophenyl)-1,3-propanediol. Yield: 2 gr; M.S. I$^+$=436.

22. (2R,3R)-2-(N-tetradecylamine)-1-(-4-adamantylacetamido-phenyl)-1,3-propanediol (AD-2754)

100 mg of compound AD-2672 were reacted with 100 mg of 1-adamantane acetic in 10 ml dichloromethane-methanol, 1:1, by the addition of 100 mg EDC. The reaction mixture was stirred with a magnetic stirrer overnight. The solution was evaporated to dryness and the resulting oil was dissolved in a mixture of 1 ml of dichloromethane and 0.5 ml methanol. This solution was loaded onto a 25×1 cm silica gel column. The compound was eluted with dichloromethane containing increasing amounts of methanol. Yield: 90 mg. M.S. I$^+$=555.

Example 2

Effect of Compound AD 2646 on Cell Viability

Effect of AD-2646 on HL60 Cells

The effect of AD-2646 on cell viability was analyzed by measuring cell mortality (viable cell count) and/or total protein quantity.

Figure 1:
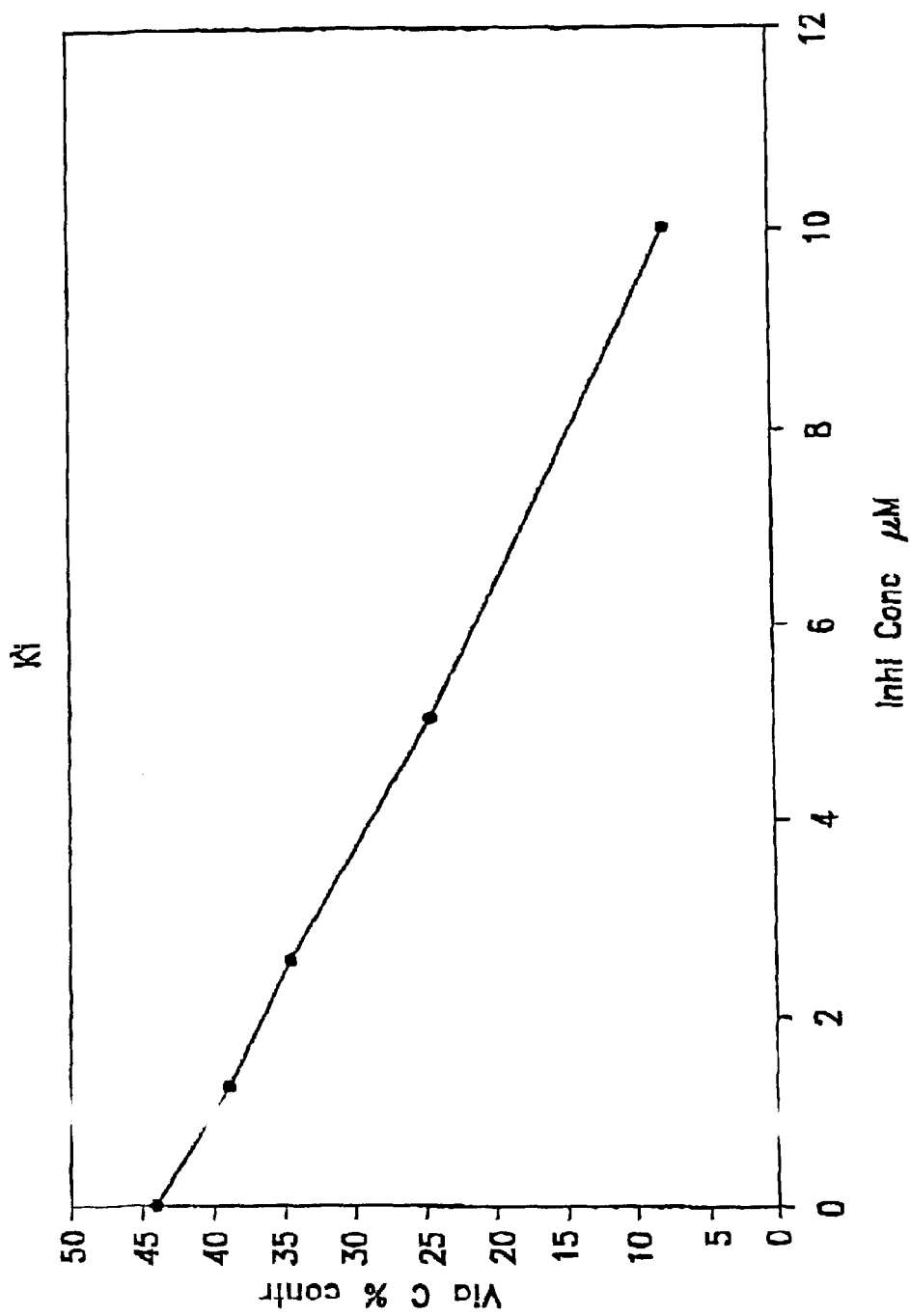
FIG. 1—Effect of AD-2646 on cell viability

HL60 cells grown in RMPI plus 10% fetal calf serum, were incubated with increasing concentrations of (2R,3R)-2-(N-tetradecylamine)-1-(4-nitro-phenyl)-1,3-propanediol (AD-2646) in 6- or 24-well dishes. The compound was added as solutions in dimethylsulfoxide (DMSO), ensuring that the concentration of this solvent did not exceed 0.1% of the volume of the culture medium. After 2 days the cells were collected, washed twice with saline, treated with trypan blue and the number of living (non-blue) cells was counted. FIG. 1 indicates an IC50 value of 5 µM.

Kinetic of the observed killing effect of the AD-2646 compound was next examined. HL60 cells were incubated with 40 μM of AD-2646 for 1, 3, 5 and 7 hours. Already after 1 hour a reduction of 60% of the viable cell number was observed.

The effect of the AD-2646 compound on cell viability was further supported when the total protein content was quantified. HL60 cells were incubated as described above, with different concentrations of AD-2646. After 2 days the cells were collected, washed twice with saline, dispersed and following a short pulsing with a probe-sonicator their protein content was quantified by the Bradford procedure. Similarly to the viable cell counting results, the protein measurements indicated an IC50 value of 5 μM.

To analyze whether the AD-2646 compound may mediate its effect on cell viability and on total protein content, in cooperation with other compounds, the cooperative effect of this compound and Taxol was next evaluated. HL60 cells were incubated for two days with 4 μM AD2646 in the presence or absence of 2 ng Taxol. As shown in Table 1, cooperation of both compounds caused significant decrease in the total protein quantity indicating a synergism between the two respective compounds.

TABLE 1

| Taxol | AD-2646 | Protein content μg |
|-------|---------|--------------------|
| +     | −       | 206                |
| −     | +       | 174                |
| +     | +       | 93                 |

Effect of AD-2646 on Different Cell Lines

In order to evaluate the generality of AD-2646 compound effect on cell viability, other cell lines were subjected to the same procedures disclosed herein above.

TSU-PR1 cells (prostate cancer cells) were incubated for two days with increasing concentrations of AD-2646. The protein content measurements shown in FIG. 2 indicate that the cells were killed with an IC50 of 6–7 μM.

Example 3
Effect of Different Compounds on Cell Viability

The effect of different compounds of the invention on cell viability was next evaluated by measuring total cell protein quantity. Different cell lines were incubated for two days in the presence of increasing concentrations of the different compounds of the present invention. The results are summarized in Table 2.

TABLE 2

Effect of different compounds on cell viability

| Compound | ell line   | C50      |
|----------|------------|----------|
| D-2673   | HL60       | 7.5 μM   |
| AD-2620  | HL60       | 3 μM     |
| AD-2687  | HL60       | 2 μM     |
| AD-2665  | MCF7-AdrR  | 7 μM     |
| AD-2665  | MCF7-NCi   | 3 μM     |

Example 4
The Apoptotic Effect of Different Compounds

In order to examine whether the observed effect on cell viability involves induction of apoptosis, the apoptotic effect of several compounds of the invention was next examined.

Myeloid, leukemic U937 cells were incubated for 24 hours in the absence or in the presence of 5 μM AD-2672 and AD-2665. Cells were then collected and the percent of apoptotic cells was determined using a kit quantifying the DEVDase, caspase 3 activity. The number of apoptotic cells incubated with AD-2672 exceeded 6-fold those in the control cells. Cells incubated with AD-2665 exceeded 2.8-fold those in the control cells.

The apoptotic effect of three different compounds was further examined on HL60 cells using a flow cytometry method. Cells were incubated with AD-2646, AD-2665 or AD-2687 at 3 and 24 hr and increasing compound concentrations, collected and washed. Washed cells were then treated with 5% Triton and stained with propidium iodide 0.5% mg in 0.1% sodium citrate pH 7.4. Analysis was performed using a Becton Dickinson Fluorescence Activated Cell Sorter (FACS).

Results of incubation for 3 hours with low concentration of the AD-2646 compound (10 μM) indicate 12% of apoptotic cells, at 20 μM 18% of the cells were apoptotic, and at 40 μM, 26% of the cells were apoptotic. Incubation for longer period (24 hours) revealed already at the lower concentration (10 μM) about 50% apoptotic cells.

Similar treatment with AD-2665 for 3 hours showed that in the low concentration (10 μM) about 8% of the cells were apoptotic, while at 20 μM this value increased to 26%. After 24 hours of incubation at 10 μM, 25% of the cells were already apoptotic.

When AD-2687 was used, after 3 hours of incubation at 15 μM, only 9% of the cells were apoptotic, while after 24 hours of incubation at a low concentration (2.5 μM), close to 50% of the cells were apoptotic.

Following a short (30 min) treatment with 40 μM of AD-2646 or AD-2665, only 5% of the cells were apoptotic.

Example 5
The Effect of Different Compound on Sphingolipid Metabolism

As described in the background of the invention, the effect of ceramide in apoptosis has been well established. Therefore, the possibility that the observed apoptotic effect of the different compounds of the invention may involve sphingolipids metabolism, was next examined.

In order to examine the effect of the different compounds on sphingolipids metabolism, different cell lines were incubated with increasing concentrations of different compounds of the invention in the presence of 2.5 μM Bodipy-C3-ceramide that was added to the culture medium as a solution in dimethylsulfoxide (not exceeding 0.1% DMSO of the final volium). After 3 hours, cells and medium were collected and centrifuged. Cells were next extracted with chloroform-methanol containing 2% acetic acid 1:1 (by volume) and the medium was shaken with an equal volume of chloroform-methanol, 1:1 (by volume). The phases were separated by centrifugation and the lower chloroform phase was collected. The solvents were evaporated and applied to thin layer chromatography silica gel plates (Whatman 4865–821) with a concentrating zone.

Plates were developed as follows: For medium: in chloroform-methanol-$H_2O$, 75:25:4 by volume. For cells: plates were first developed with chloroform-methanol, 9:1, then dried and re-run in chloroform-methanol: $H_2O$, 65:35:4.

Standards of Bodipy-C3-ceramide: Bodipy-C3-glucosylceramide (Bod3-GC) and Bodipy C3 sphingomyelin (Bod3-SPM) were used as markers. The fluorescence of the respective Bod3-SPM and Bod3-GC spots was quantified using a Fuji FLA-2000 scanner.

Generally, results indicated that Bod3-SPM was present both in the cells and medium, whereas Bod3-GC was present practically only in the cells.

As shown in Table 3, incubation of HL60 cells with different concentrations of AD-2646 resulted in reduction of the Bod3-SPM (cell+medium), with IC50 values of about 6 $\mu$M (FIG. 3), while the IC50 for Bod3-GC reduction was about 12 $\mu$M (FIG. 4).

The effect of AD-2646 on sphingolipid metabolism was further examined using TSU-PR1 prostate cancer cells. Results showed reduction of Bod3-SPM had IC50 values of about 5 $\mu$M (FIG. 5).

TABLE 3

Effect of different compounds of the invention on metabolism of sphingolipids

| ell line | ompound | od 3-SPM | od 3-GC |
|---|---|---|---|
| HL60 | AD-2646 | 6 $\mu$M | 12 $\mu$M |
| MCF-NCi | AD-2665 | 7 $\mu$M | 10 $\mu$M |
| HL60 | AD-2673 | 6 $\mu$M | 2.5 $\mu$M |
| HL60 | AD-2672 | 4 $\mu$M | 10 $\mu$M |
| HL60 | AD-2665 | 4 $\mu$M | 5 $\mu$M |
| HL60 | AD-2687 | 4 $\mu$M | 12 $\mu$M |

Comparison of the effect of the different compounds on synthesis of Bod3-SPM and Bod3-GC was next examined. HL60 cells were incubated with the different compounds AD-2672, AD-2673 and AD-2674, each at 5 and 10 $\mu$M.

FIG. 6 is a fluorescent image, indicating that AD-2672 strongly reduces the level of Bod3-SPM but not of Bod3-GC. In contrast, AD-2673 and AD-2674 at 10 $\mu$M show a low inhibition of Bod3-SPM but a much stronger reduction of the level of Bod3-GC.

Effect of Drug Sensitivity of Cells on the Metabolism of Sphingolipids

Breast cancer cells, MCF-NCi (drug-sensitive) and MCF-AdrR (Adriamycin-resistant) were incubated with Bod-C3-ceramide for 1,2,4 and 8 hours, and the Bod-C3-SPM and Bod-C3-GC in the respective cells and medium were quantified. In the drug-sensitive cells, the Bod-C3-SPM and Bod-C3-GC in the cells exceeded the quantity in the medium 3–4-fold and 6-fold, respectively. Surprisingly, the respective values in the adriamycin resistant cells were significantly different, quantities of Bod-C3-SPM as well as Bod-C3-GC secreted into the drug-resistant cell medium were higher by 5–9-fold of those secreted by their drug-sensitive counterparts.

Example 6
Inhibitory Effect of AD-2144 on Sphingomyelinases

N-hexyl-sphingosyl phosphorylcholine (AD-2144) was tested as to its inhibitory effect on sphingomyelinases, acidic (i.e., with an optimum at about pH 5) or neutral (with a pH optimum at about pH 7.4). For this purpose a sonicate of HL60 leukemic cells was used as enzyme source. Increasing concentrations of AD-2144 were dispersed by a mixture of fluorescent and non-fluorescent sphingomyelin (Bodipy-C12-SPM:SPM, 1:19), buffer and 0.25% Triton-X100 in a volume of 100 $\mu$l. For acid sphingomyelinase 0.4M acetate buffer pH 5.0 was used; for neutral sphingomyelinase 0.2M Tris buffer, pH 7.4 and 5 mM magnesium chloride. To 100 $\mu$l of these dispersions, 100 $\mu$l of HL60 cells sonicate were added. Incubation was 2–3 hours after which 0.8 ml of chloroform:methanol 2:1 were added, stirred and the lower, chloroform phase was collected, dried and applied to a thin layer chromatography plate. The plate was developed in a mixture of chloroform and methanol, 87:3. The fluorescence of the product, i.e., Bodipy-C12-ceramide, was quantified.

For acid sphingomyelinase as well as for neutral spingomyelinase: at 300 $\mu$M of AD-2144 there was a reduction of over 60% in Bodipy-C12-ceramide. Table 4 shows reduction of the Bodipy-C12-ceramide by the AD-2144 compound.

TABLE 4

AD-2144 causes reduction of Bodipy-C12-ceramide

| AD-2144 Concentration | % reduction in Bodipy-C12-ceramide |
|---|---|
| 50 $\mu$l | 30 |
| 100 $\mu$l | 44 |
| 150 $\mu$l | 65 |
| 300 $\mu$l | 82 |

Example 7

In vivo Toxicity of AD-2646

As shown in the previous Examples, the AD-2646 compound displays significant specific cell mortality by inducing apoptotic mechanism. This apoptotic phenomenon is probably mediated by inhibition of sphingolipids metabolism. In order to evaluate the potential use of such compound as specific anti-proliferative drug, an in vivo toxicity study was performed in mice.

Six groups, each of 5 Swiss mice were injected, intraperitoneally with solutions of AD-2646, at varying concentrations, each in a volume of 100 $\mu$l. Injections were performed on days 1, 2, 3, 4, and mice viability was tested (Table 5).

As shown in Table 5, only a very high concentration of AD-2646 was toxic.

TABLE 5

AD-2646 viability test

| AD-2646 Concentration | No. of mice in each day | | | | | |
|---|---|---|---|---|---|---|
| | 1 | 2 | 3 | 4 | 5 | 6 |
| 0 | 5 | 5 | 5 | 5 | 5 | 5 |
| 1 mg/kg | 5 | 5 | 5 | 5 | 5 | 5 |
| 5 mg/kg | 5 | 5 | 5 | 5 | 5 | 5 |
| 10 mg/kg | 5 | 5 | 5 | 5 | 5 | 5 |
| 25 mg/kg | 5 | 5 | 5 | 5 | 5 | 5 |
| 50 mg/kg | 5 | 5 | 4 | 3 | 2 | 1 |

Example 8

2×10$^5$ Leishmania major promastigote cell, each in a volume of 100 $\mu$l were added to 100 $\mu$l medium (RPMI 1640 culture medium complemented with 20% FCS, 1% penicillin and 1% streptomycin) in 96-well plates containing zero and increasing concentrations of (2S,3R)-2-N-aminohexyl-1-(4-N-hexylaminophenyl)-1,3-propanediol (AD-2663) in 2-fold serial dilution. After incubation period (3 h, 27° C.) the number of cells was determined by counting on aliquot from each well on a Neulander cell counter under a microscope. The IC50 for cell reduction was 7 $\mu$M.

What is claimed is:

1. Compounds of the general formula (1):

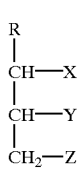  (I)

wherein R represent a linear or branched, saturated, or unsaturated alkyl or alkenyl chain, which may optionally be substituted by hydroxyl, $CH_3(CH_2)_m CH=CH-$, $CH_3(CH_2)_m$, wherein m is zero or an integer of from 1 to 20, phenyl, optionally substituted by nitro, amino, alkylamino, acylamino, —NHC(S)NH-alkyl, sulfonylamido-alkyl, a group

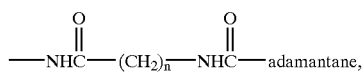

wherein n is an integer of from 1 to 20, or a group —NH-adamantane, —NH-t-BOC, —NH—FMOC or NH—CBZ;

X represents hydrogen or the group —$OR_4$ in which $R_4$ is hydrogen or a linear or branched, saturated or unsaturated $C_1$–$C_6$ alkyl or alkenyl chain which may be optionally substituted with hydroxy;

Y represents —$NH_2$, $NHR^x$ wherein $R^x$ is hydrogen, a linear or branched alkyl or alkenyl chain which may be optionally substituted with hydroxy, an amino protecting group,

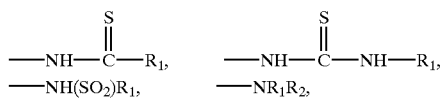

—$N^+R_1R_2R_3$, wherein $R_1$, $R_2$ and $R_3$, which may be identical or different each represent $C_{1-6}$alkyl or $C_{1-6}$alkenyl, a group

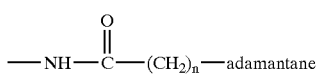

wherein n is zero or an integer of from 1 to 20, a group —NH-adamantane, a group

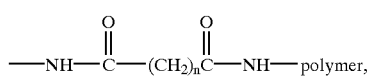

where "polymer" designates a natural or synthetic biocompatible polymer having a molecular weight between $10^3$ and $10^6$ daltons;

Z represents hydrogen, —OH, a mono- or disaccharide, a monosaccharide sulfate and choline phosphate;

with the proviso that

Y cannot represent $NH_2$ when R represents an alkyl, the group $CH_3(CH_2)_m CH=CH-$, phenyl or nitro phenyl; and Y cannot represent the groups —$NR_1R_2$ or —$N^+R_1R_2R_3$, or $NHR_4$ where $R_4$ represents octyl when $R_1$ represents a methyl, R represents the group $CH_3(CH_2)_m CH=CH-$ and Z represents —OH;

and isomers and pharmaceutically acceptable salts thereof.

2. A compound according to claim 1, wherein Y is —$NH_2$ or $NHR_x$.

3. A compound according to claim 1 or claim 2, wherein R is nitrophenyl.

4. A compound according to any one of claims 1 or 2, wherein R is aminophenyl or alkylaminophenyl.

5. A compound according to any one of claims 1 to 4, wherein Z is —OH.

6. A compound according to any one of the preceding claims wherein said amino protecting group is selected from tBOC, FMOC and CBZ.

7. A compound according to claim 1, being the compound:

(designated AD-2665)

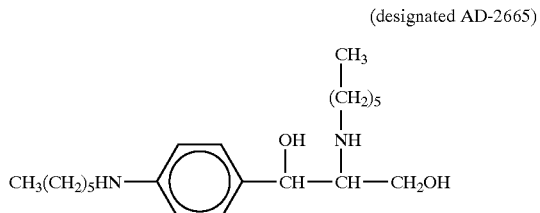

(designated AD-2687)

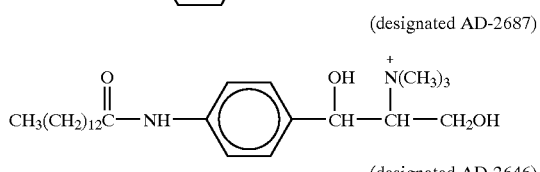

(designated AD-2646)

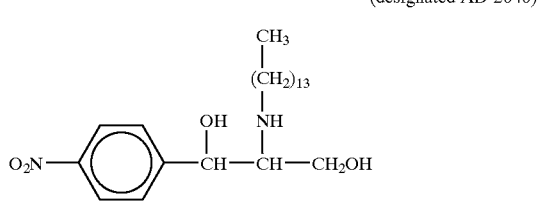

(designated AD-2672)

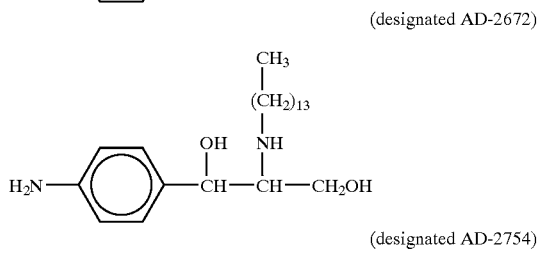

(designated AD-2754)

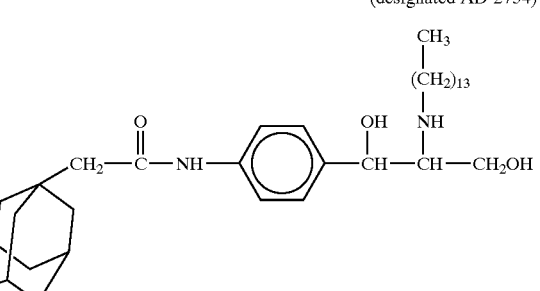

(designated AD-2673)

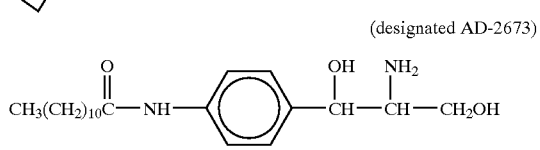

-continued (designated AD-2144)

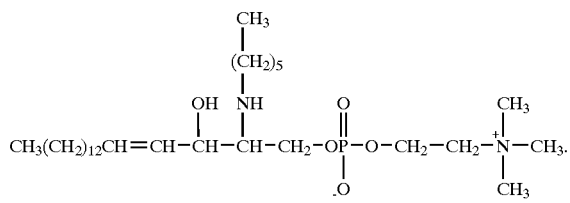

8. A pharmaceutical composition comprising as active ingredient a compound of formula (I) wherein the substituents are as defined in claim 1, and optionally further comprising pharmaceutically acceptable carrier, adjuvant or diluent.

9. A pharmaceutical composition according to claim 8, for reducing accumulation of sphinglipids.

10. A pharmaceutical composition according to claim 9, for the treatment of a lipid storage disease.

11. A pharmaceutical composition according to claim 10, wherein said lipid storage disease is selected from Gaucher disease, Tay-Sachs disease, Niemann-Pick disease, Krabbe disease, Metachromatic leukodystrophy, Fabry disease and Farber disease.

12. Use of a compound of formula (I) wherein the substituenits are as defined in claim 1 as an inhibitor of any one of acidic, neutral and alkaline sphingomyelinases, acidic, neutral and alkaline ceramidases, α-galactosyl synthetase, ceramide synthetase, sphingomyelin synthetase and glycoceramides synthetase.

13. A pharmaceutical composition according to claim 8, for the treatment of cancerous diseases.

14. Use of a compound of formula (I) wherein the substituents are as defined in claim 1, for killing of wild type and drug-resistant cancer cells.

15. Use according to claim 14, for the selective killing of drug-resistant cancer cells.

16. A pharmaceutical composition according to claim 8, for the treatment of parasitic, viral, bacterial, fungal and prion diseases.

17. A pharmaceutical composition according to claim 16, wherein said parasitic disease is malaria or leishmania.

18. Use of a compound of formula (I) wherein the substituents are as defined in claim 1, as an antimalarial or antileishmanial agent.

19. A method of treating a lipid storage disease in a patient in need of such treatment comprising administering to said patient a therapeutically effective amount of a compound of formula (I) wherein the substituents are as defined in claim 1 or of pharmaceutical composition comprising the same.

20. A method according to claim 19, wherein said lipid storage disease is selected from Gaucher disease, Tay-Sachs disease, Niemann-Pick disease, Krabbe disease, Metachromatic leukodystrophy, Fabry disease and Farber disease.

21. A method of treating a cancerous disease in a patient in need of such treatment comprising administering to said patient a therapeutically effective amount of a compound of formula (I) wherein the substituents are as defined in claim 1 or of pharmaceutical composition comprising the same.

* * * * *